(12) United States Patent
Okiyama

(10) Patent No.: US 8,585,661 B2
(45) Date of Patent: Nov. 19, 2013

(54) MIXTURE INJECTION PORT

(75) Inventor: Tadashi Okiyama, Hiroshima (JP)

(73) Assignee: JMC Co., Ltd., Hiroshima (JP)

( * ) Notice: Subject to any disclaimer, the term of this patent is extended or adjusted under 35 U.S.C. 154(b) by 964 days.

(21) Appl. No.: 10/559,533

(22) PCT Filed: Jul. 8, 2004

(86) PCT No.: PCT/JP2004/009732
§ 371 (c)(1),
(2), (4) Date: Dec. 2, 2005

(87) PCT Pub. No.: WO2005/004973
PCT Pub. Date: Jan. 20, 2005

(65) Prior Publication Data
US 2006/0184140 A1    Aug. 17, 2006

(30) Foreign Application Priority Data

Jul. 9, 2003   (JP) .................................. 2003-194604
Jun. 21, 2004  (JP) .................................. 2004-183044

(51) Int. Cl.
*A61M 5/00*   (2006.01)

(52) U.S. Cl.
USPC ....................................................... 604/249

(58) Field of Classification Search
USPC ............ 251/149, 149.1, 149.5; 604/201, 246, 604/248, 249, 256, 523, 533, 537, 86, 88, 604/93.01, 905; 137/808, 812
See application file for complete search history.

(56) References Cited

U.S. PATENT DOCUMENTS

| | | | |
|---|---|---|---|
| 3,880,401 A * | 4/1975 | Wiltse ........................... | 251/205 |
| 4,141,379 A * | 2/1979 | Manske ........................ | 137/496 |
| 4,197,848 A * | 4/1980 | Garrett et al. .................. | 604/19 |
| 4,387,879 A   | 6/1983 | Tauschinski | |
| 4,601,703 A * | 7/1986 | Herlitze ........................ | 604/86 |

(Continued)

FOREIGN PATENT DOCUMENTS

| | | |
|---|---|---|
| EP | 1190735 A1 | 3/2002 |
| JP | 54142888   | 11/1979 |

(Continued)

OTHER PUBLICATIONS

Japanese Office Action, and partial English translation, dated Oct. 28, 2008, in corresponding Japanese Application No. 2005-511525, 4 pp.

(Continued)

*Primary Examiner* — Kevin C Sirmons
*Assistant Examiner* — Imani Hayman
(74) *Attorney, Agent, or Firm* — Pillsbury Winthrop Shaw Pittman LLP

(57) ABSTRACT

A mixed injection port capable of suppressing the continuous accumulation of medical fluid or blood therein and allowing efficient internal cleaning, wherein a recirculation part (140) is formed at a step between an inner cavity (114) and a thin tube part (117). Even if the fluid is accumulated in a clearance area (1141) produced in the inner cavity (114) when a lure is inserted into a slit (131), the fluid can be securely replaced with the fluid newly flowing therein through a septum (130) and the continuous accumulation of the fluid can be suppressed. A more efficient internal cleaning can be realized by installing a fluid accumulation prevention part such as an annular rib between the septum (130) and the inside wall of the inner cavity (114) and burying the clearance area (1141).

17 Claims, 18 Drawing Sheets

(56) References Cited

U.S. PATENT DOCUMENTS

| | | | |
|---|---|---|---|
| 4,683,916 A | 8/1987 | Raines | 137/854 |
| 5,116,021 A | 5/1992 | Faust et al. | 251/149 |
| 5,242,393 A * | 9/1993 | Brimhall et al. | 604/86 |
| 5,441,487 A * | 8/1995 | Vedder | 604/167.03 |
| 5,520,661 A | 5/1996 | Lal et al. | |
| 5,775,671 A * | 7/1998 | Cote, Sr. | 251/149.8 |
| 5,817,069 A * | 10/1998 | Arnett | 604/256 |
| 5,957,898 A | 9/1999 | Jepson et al. | |
| 5,961,497 A * | 10/1999 | Larkin | 604/246 |
| 6,158,458 A * | 12/2000 | Ryan | 137/515.5 |
| 6,193,697 B1 * | 2/2001 | Jepson et al. | 604/201 |
| 6,595,964 B2 * | 7/2003 | Finley et al. | 604/246 |
| 2002/0002351 A1 | 1/2002 | Cote, Sr. et al. | |
| 2002/0193752 A1 | 12/2002 | Lynn | |
| 2005/0171510 A1 * | 8/2005 | DiCarlo et al. | 604/537 |

FOREIGN PATENT DOCUMENTS

| | | |
|---|---|---|
| JP | S57-122889 | 7/1982 |
| JP | 06047093 | 2/1994 |
| JP | 10500345 | 1/1998 |
| JP | 10-127778 | 5/1998 |
| JP | 2000515797 A | 11/2000 |
| JP | 2002-095758 | 4/2002 |
| JP | 2002177365 | 6/2002 |
| JP | 2002-191583 | 7/2002 |
| JP | 2003038658 | 2/2003 |
| WO | WO 95/15193 | 6/1995 |
| WO | 9534341 A1 | 12/1995 |
| WO | 9852631 A1 | 11/1998 |
| WO | WO 99/58186 | 11/1999 |

OTHER PUBLICATIONS

Office Action Dated Feb. 23, 2009 for Japanese Patent Application No. 2005-511525.

European Search Report dated Jan. 22, 2013.

* cited by examiner

Intracatheter

|  | Amount of remaining bovine blood (μL) | Amount of remaining fat emulsion (μL) |
|---|---|---|
| Circulating portion and annular rib | 0.15 | 0.21 |
| Circulating portion alone | 1.09 | 1.25 |
| None of them | 18.02 | 20.34 |

FIG. 15

MIXTURE INJECTION PORT

This is the U.S. National Phase of International Application No. PCT/JP2004/009732, filed Jul. 8, 2004, which relies for priority upon Japanese Patent Application Nos. 2003-194604, filed Jul. 9, 2003, and 2004-183044, filed Jun. 21, 2004, the contents of all of which are incorporated herein by reference in their entireties.

TECHNICAL FIELD

The present invention relates to a mixture injection port, in particular, a mixture injection port into/from which a luer or the like can be inserted/removed and that is used as a medical connector.

BACKGROUND ART

A mixture injection port may be provided as a medical connector between an intracatheter inserted to a blood vessel of a patient and an infusion solution bag, a syringe or the like in which a fluid such as blood or an infusion solution is stored for intravenous nutrition, blood transfusion, blood collection or the like. This mixture injection port is provided with a channel tube through which a fluid such as high calorie infusion solution or blood flows in its inside, and is provided between a tube member such as a luer or a cannula connected to a storing portion in which a medical liquid is stored, such as an infusion solution bag and a syringe, and an extension tube connected to, for example, an intracatheter. One end of the channel tube is covered with a septum having a slit into which the tube member is inserted so that a medical liquid in the storing portion is infused to the body of a patient while the member such as a luer is inserted and fixed in the slit.

JP2002-191583A discloses an example of a connector (injection site) that is provided between a puncture needle and a cannula, a luer or the like at the time of collecting blood of a patient as an example of a medical connector used in the above-described cases and a cannula device. Hereinafter, such a conventional technique will be described.

FIG. 1 is a cross-sectional view of a connector of a conventional technique.

As shown in FIG. 1, in a connector 900, one end of a channel tube 910 is covered by a septum 920 made of an elastic material such as rubber and provided with a slit 921, and the other end (second end) of the channel tube 910 is attached to an intracatheter pieced to, for example, a blood vessel of a patient via an extension tube (both not shown). A medical liquid is poured into the channel tube 910 from a cannula 990 inserted into the slit 921 of the septum 920, and infused to a patient through the second end of the channel tube 910.

When the cannula 990 is removed from the septum 920 at the end of the infusion, the slit 921 portion is automatically closed by the elasticity of the septum 920 to prevent microorganisms such as bacteria from entering the inner cavity 930 of the channel tube 910 from the outside and from being grown (see JP2002-191583A).

Thus, even if the cannula 990 is removed, the inner cavity 930 of the connector is not exposed to external air, so that penetration of microorganisms can be suppressed and their growth can be suppressed.

DISCLOSURE OF INVENTION

Problem to be Solved by the Present Invention

In the conventional connector 900, with the insertion of the cannula 990, the septum 920 is bended in the direction of its insertion. To prevent the bended septum 920 from pressing against the cannula 990 so that the cannula 990 cannot be inserted smoothly, the inner cavity 930 is wide for the purpose of reducing insertion resistance of the cannula 990 by accommodating the bended septum 920.

Therefore, a part of the medical liquid ejected from the cannula 990 tends to stay and stagnate in an area 932 on the septum 920 side in the inner cavity 930. The medical liquid that has stagnated in the area 932 is hardly replaced by newly injected medical liquid even if the cannula 990 is removed and the cannula 990 is inserted again for the next infusion to inject the medical liquid, because the area 932 is away from the tip of the cannula 990 and is positioned opposite to the fluid injection direction. Therefore, some microorganisms enter, and when the medical liquid is fat emulsion or other substances that are suitable to growth of microorganisms, it is possible that microorganisms are grown in the area 932.

Furthermore, the fact that the medical liquid is hardly replaced in the area 932 may cause a problem at the time of collecting blood. In general, after blood is collected with a cannula or a luer that is inserted into the mixture injection port, a heparin solution is injected thereto for cleaning in order to prevent blood from coagulating in the inner cavity or the like. However, in the area 932, blood is not replaced sufficiently by the injected heparin solution, as described above, and the blood may remain and microorganisms may be grown there.

In view of the above-described problem, the present invention has an object of providing a mixture injection port that can suppress continuous stagnation of a medical fluid or blood inside and providing a mixture injection port that allows the inner cavity to be cleaned efficiently.

Means for Solving the Problem

In order to solve the above-described problem, a first mixture injection port of the present invention in which one end of a channel tube is covered by a septum provided with a slit into which a tube member is inserted, wherein the channel tube is provided with a circulating portion for circulating a medical fluid injected from the inserted tube member to the septum side and then guiding the fluid to the downstream side of the channel tube.

With this configuration, a fluid such as a medical fluid or blood injected from a tube member is circulated to the septum side where conventionally the fluid was hardly replaced, so that the medical fluid or the like that stagnates in a region on the septum side when the tube member is removed temporarily and inserted at the next time can be replaced by a new fluid reliably. Therefore, in the internal portion of the channel tube, a medical fluid, blood or the like is suppressed from remaining continuously. As the tube member, for example, a luer or a cannula can be used.

The channel tube may include a body portion whose opening is covered by the septum and that is provided with an inner cavity that is a space for accommodating the septum that is deformed by the insertion of the tube member, and a leg portion that is provided with a narrow tube portion having a smaller width than that of the inner cavity and that is in communication from the inner cavity to the other end of the channel tube, and the circulating portion has a circulating-plate portion that is mounted on a step generated between the inner cavity and the narrow tube portion. With this configuration, it is convenient to provide the circulating portion inside the inner cavity.

Herein, a groove extending in a direction different from a direction from which a medical fluid is injected from a position with which the top of the inserted tube member is in contact or a position near the top may be formed on a surface on the inner cavity side of the circulating-plate portion, and a medical fluid flown in from the top of the tube member may be allowed to flow along the groove, so that the direction in which the fluid travels is changed. This configuration is preferable in order to circulate the fluid, for example, in a configuration where the top of the tube member is in contact with the circulating-plate portion to position the tube member such as a luer.

The circulating-plate portion may be provided with a holding portion on its back face that is engaged with the narrow tube portion and holds the circulating portion inside the channel tube. With this configuration, it is easy to position the circulating portion. It is possible to provide the circulating portion without this holding portion. When the holding portion is provided, it is preferable that a groove for guiding a medical fluid circulated to the septum side from the inner cavity to the narrow tube portion is formed in the back face of the circulating-plate portion and the holding portion in order to guide the fluid to the downstream of the channel.

The circulating portion may be provided with an edge portion that protrudes toward the septum in the edge of the circulating-plate portion. With this configuration, the medical fluid or other fluid that stagnates in a gap region generated between the septum and the inner cavity can be replaced more reliably.

In this case, it is preferable that a groove for guiding the medical fluid circulated to the septum side from the inner cavity to the narrow tube portion is formed on the outer circumferential surface of the edge portion in order to guide the fluid circulated to the septum side to the downstream of the channel.

A second mixture injection port of the present invention in which one end of a channel tube is covered by a septum provided with a slit into which a tube member is inserted, wherein a fluid-stagnation-preventing portion is provided for filling a gap region generated between an inner wall of an inner cavity formed inside the channel tube and the septum that has been deformed to the inner cavity side by insertion of the tube member, when the tube member is inserted into the slit.

With this configuration, a gap that has been generated between the septum and the inner wall of the channel tube can be prevented from being generated when the tube member is inserted into the septum, and thus the fluid is suppressed from remaining inside the mixture injection port. Therefore, the fluid does not remain after a flush-cleaning treatment is performed with a detergent such as heparin or a physiological saline solution, and thus more efficient internal cleaning can be achieved.

The fluid-stagnation-preventing portion may be formed integrally with the septum. With this configuration, the number of components can be decreased and the mixture injection port of the present invention can be produced in a simple manner. The fluid-stagnation-preventing portion may be a rib provided such that at least one portion of its outer circumference and its top is in contact with the inner wall throughout its entire circumference. With this configuration, the sealing performance between the septum and the inner wall of the channel tube can be increased, so that the present invention is also preferable when used, not only for infusion and blood transfusion, but also for blood collection. In this case, the septum is generally made of an elastic material, so that the rib has elasticity in the direction in which the rib presses the inserted tube member, and therefore has a function of increasing the sealing performance between the septum and the tube member.

The fluid-stagnation-preventing portion may be provided, not only on the septum side, but also provided so as to protrude from the inner wall and be in contact with the septum. The shape of the fluid-stagnation-preventing portion in this case can be, for example, semi-spherical, wedged-shaped or in other various shapes, as described later.

In the second mixture injection port, it is preferable that the inner cavity is provided with a circulating portion for circulating a medical fluid injected from the inserted tube member to the septum side then guiding the fluid to the downstream side of the channel tube. This is because, as in the first mixture injection port of the present invention, when a detergent such as heparin or a physiological saline solution is injected from the tube member for flush-cleaning, the detergent reaches the septum more reliably, and more efficient internal cleaning can be achieved.

Here, the channel tube may provided with a narrow tube portion having a smaller width than that of the inner cavity and that is in communication from the inner cavity to the other end of the channel tube, and the circulating portion may have a circulating-plate portion that is mounted on a step generated between the inner cavity and the narrow tube portion. This configuration is preferable for providing the circulating portion inside the inner cavity. In order for the detergent to reach more reliably the region between the septum and the inner wall of the inner cavity, it is more preferable that an edge portion that protrudes toward the septum is provided in the edge of the circulating-plate portion, which is the same as in the first mixture injection port.

A method for transferring a fluid of the present invention is a method for transferring a fluid to/from a body using a mixture injection port in which one end of a channel tube is covered by a septum provided with a slit into which a tube member is inserted, wherein either one of the first and the second mixture injection ports of the present invention is used.

Here, as a medium for storing the fluid, a syringe, a bag or the like can be used. As the member for forming the fluid channel that is introduced to the body, for example, an extension tube as described above can be used, and this is not necessarily included in the mixture injection port of the present invention. The infusion method of the present invention is effective to animals other than human beings.

Effect of the Invention

According to the first mixture injection port of the present invention, a circulating path for guiding a fluid to a portion in which a fluid stagnates (septum side) is formed, so that a fluid is circulated to the septum side in which conventionally a fluid was hardly replaced and can be replaced by a new fluid reliably. Therefore, in the channel tube, a fluid is suppressed from stagnating continuously. For example, when used for infusion, blood collection or the like, even if a medical fluid, blood or the like stagnates in the inner cavity of the mixture injection port, the medical fluid or the like can be replaced reliably by a newly transferred fluid. Therefore, an effect of suppressing continuous stagnation of medical fluid, blood or the like can be provided.

According to the second mixture injection port of the present invention, a fluid-stagnation-preventing portion is provided in the portion in which a fluid stagnates (septum side), so that there is no portion in which a fluid stagnates continuously in the channel tube, and therefore such stagnation can be suppressed. For example, when used for infusion, blood collection or the like, the fluid-stagnation-preventing portion suppresses generation of a gap region generated between the inner wall of the inner cavity formed inside the mixture injection port and the septum that has been deformed to the inner cavity side when a tube member such as a luer or a cannula is inserted, and therefore an effect of suppressing stagnation of a fluid such as intravenous hyperalimentation solution or blood can be provided.

BRIEF DESCRIPTION OF DRAWINGS

FIG. 15 is a table showing the results of tests regarding the effect when, in addition to the circulating portion 140, an annular rib 133 is provided in the septum 130 in the fourth embodiment.

BEST MODE FOR CARRYING OUT THE INVENTION

Hereinafter, embodiments of the present invention will be described with reference to the accompanying drawings.

Embodiment 1

First, a first embodiment of the present invention will be described.

<Overall Configuration of a Mixture Injection Port>

Figure 1:
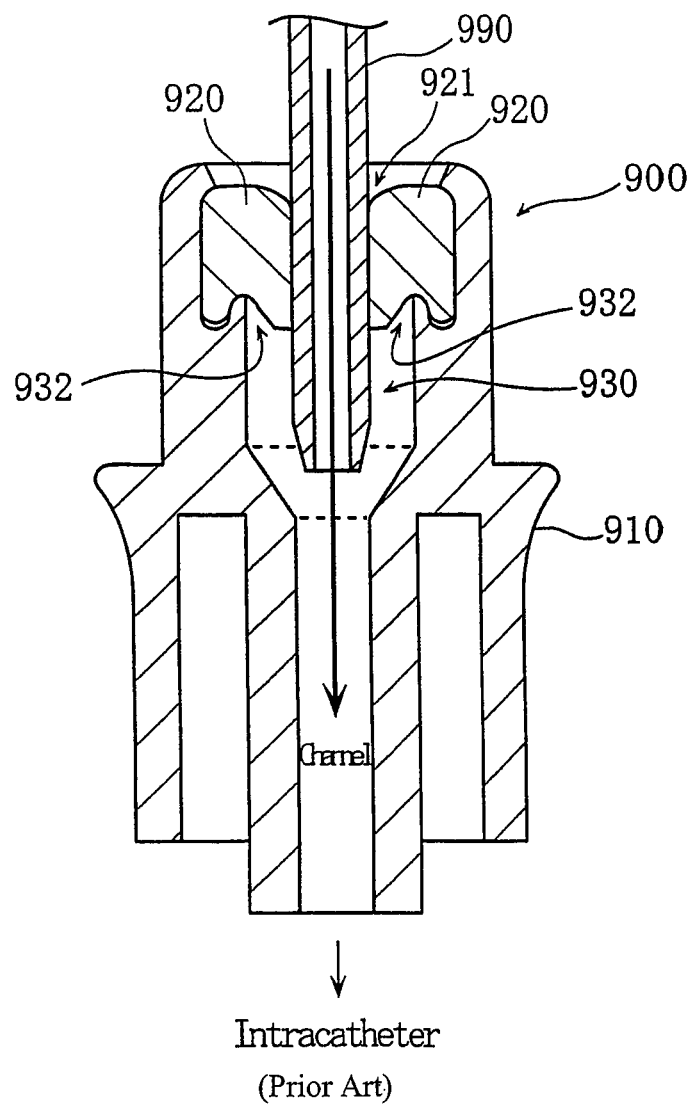
FIG. 1 is a cross-sectional view for illustrating a configuration of a conventional connector.
Figure 2:
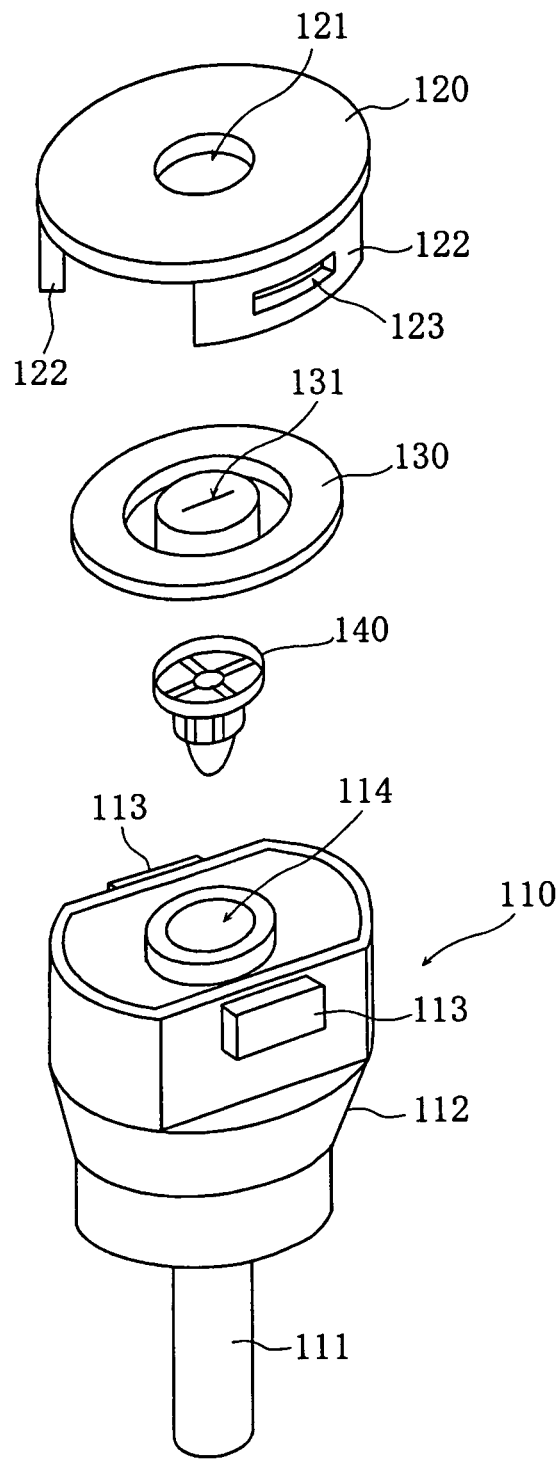
FIG. 2 is an exploded perspective view for illustrating a configuration of a mixture injection port of a first embodiment of the present invention.
Figure 3:
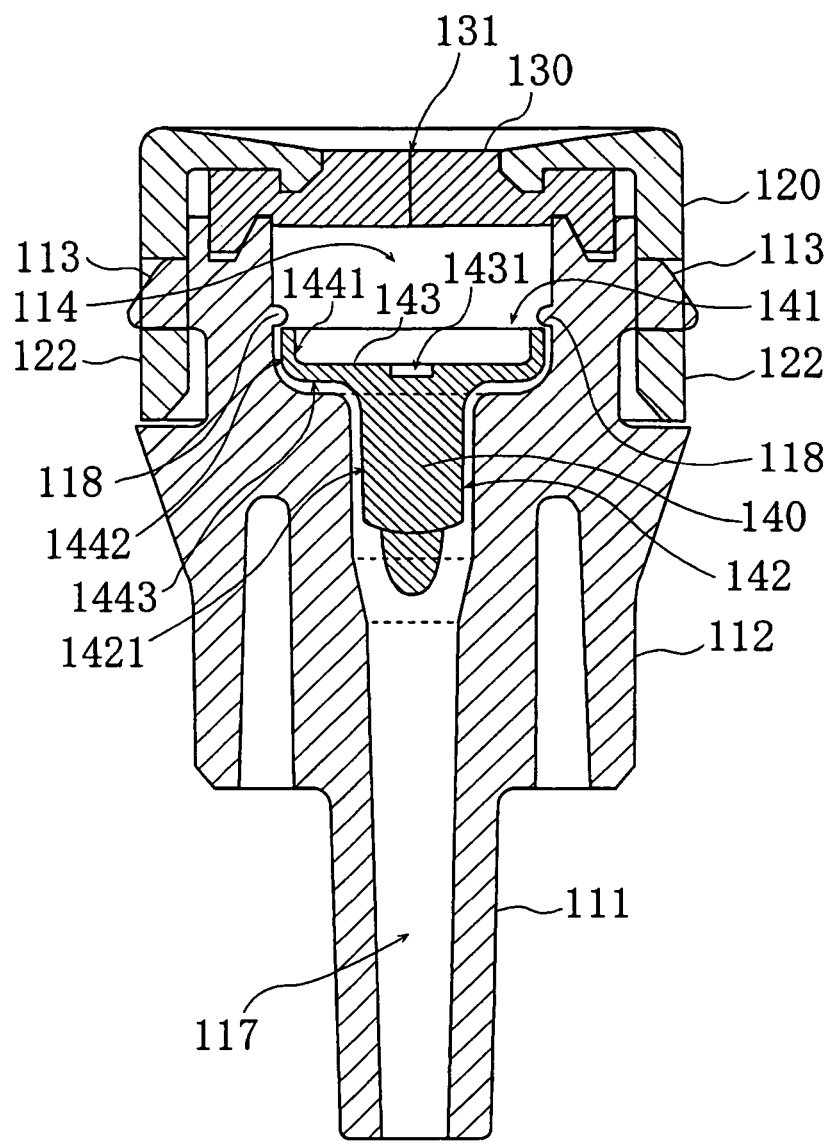
FIG. 3 is a cross-sectional view of a mixture injection port of the first embodiment.
Figure 4:
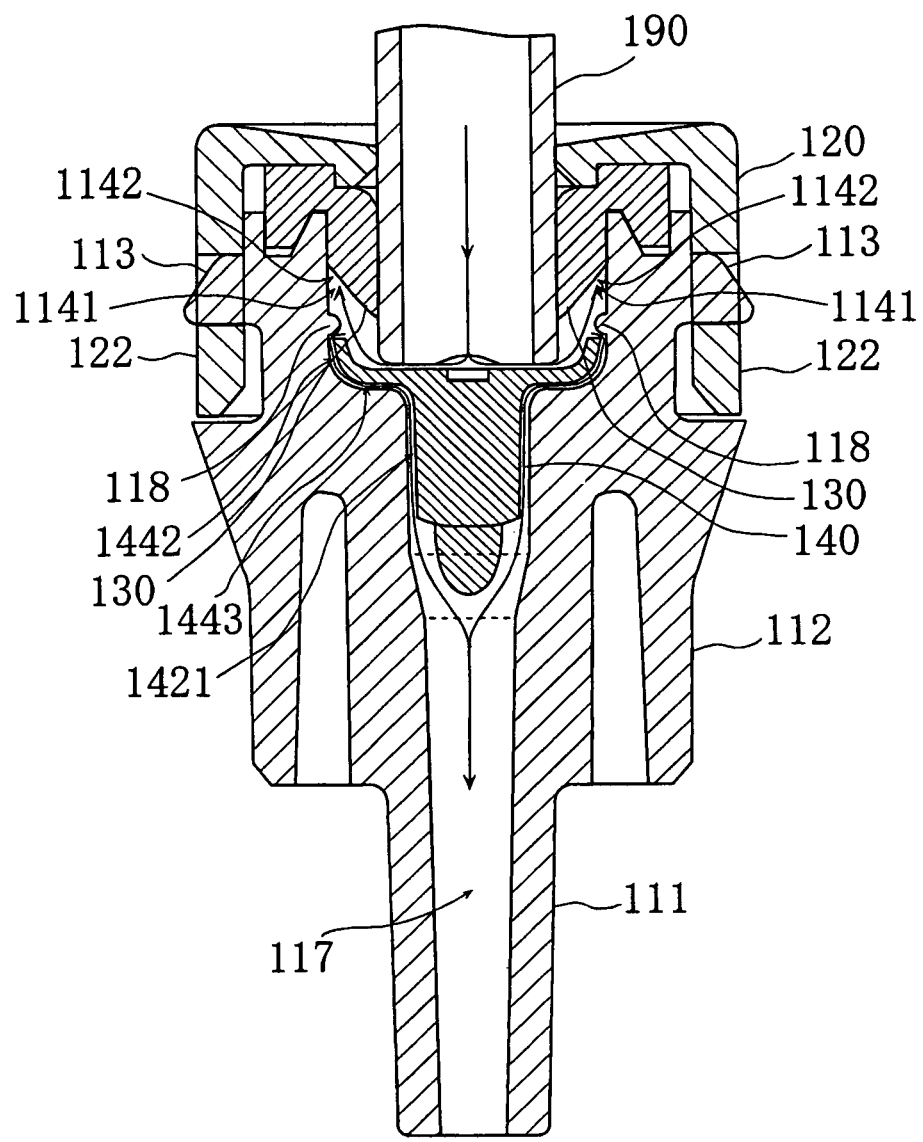
FIG. 4 is a cross-sectional view showing the state in which a luer is inserted into the mixture injection port of the first embodiment.

FIG. 2 is an exploded perspective view of a mixture injection port of a first embodiment of the present invention, and FIGS. 3 and 4 are cross-sectional views of the mixture injection port. In the cross-sectional views referred to in this specification, for easy understanding of the drawings, in some areas, the background of the cross section is not drawn, and only the end face is shown.

As shown in FIG. 2, the mixture injection port includes a channel tube unit 110, a circulating portion 140, a septum 130, and a cap unit 120. The circulating portion 140 is inserted into the inner cavity 114 of the channel tube unit 110, and the cap unit 120 is engaged with and fixed to one end of the channel tube unit via the septum 130 so that the opening of the inner cavity 114 is sealed.

As shown in FIG. 2, the channel tube unit 110 includes a leg portion 111 and a body portion 112 and is formed such that the inner cavity 114 and a narrow tube portion 117 that passes through the leg portion 111 and has a smaller width than that of the inner cavity 114 are in communication with each other, as shown in FIGS. 3 and 4.

An extension tube or the like (not shown) is attached to the outer circumference of the leg portion 111, and a luer 190 (see FIG. 4) is inserted to the inner cavity 114. When a fluid such as a medical liquid is injected therefrom, the fluid is infused to a patient from the inner cavity 114 through the narrow tube portion 117 in the leg portion 111 via the extension tube or the like.

In the channel tube unit 110, an annular protrusion 118 (see FIG. 3) for regulating the position of the circulating portion 140 is formed in the inner circumferential wall of the inner cavity 114, and a pair of engagement protrusions 113 for engaging and fixing the cap unit 120 is formed on the outer circumference thereof on the inner cavity 114 side (FIG. 2).

The circulating portion 140 is made of rigid plastic having an excellent chemical resistance, and is held by being engaged with a step between the inner cavity 114 and the narrow tube portion 117 to block flow of the fluid such as a medical liquid injected from the luer 190 so that the fluid flows toward the septum 130 side and is circulated in the inner cavity 114.

As shown in FIG. 2, the septum 130 is formed of a disk-like elastic material made of isoprene rubber, silicon rubber or the like, is provided with a slit 131 on its center and is fixed to the end portion of the channel tube unit 110 on the inner cavity 114 side by the cap unit 120 such a manner that the inner cavity 114 is closed. This slit 131 is generally closed by being pressed by the elasticity of the septum 130. However, when the luer 190 is inserted, the septum 130 in the vicinity of the slit 131 is bended in the insertion direction so that the slit is opened while keeping a substantially airtight state.

In the cap unit 120, a pair of engaging portions 122 having engaging holes 123 is provided in a disk-like member, in the center of which a hole 121 is opened opposed to the slit 131 of the septum 130, and the engaging holes 123 in the engaging portions 122 are engaged with the engaging protrusions 113 of the channel tube unit 110, so that the septum 130 is engaged with and fixed to the channel tube unit 110 while they are pressed against each other.

<Configuration of the Circulating Portion 140>

Figure 5:
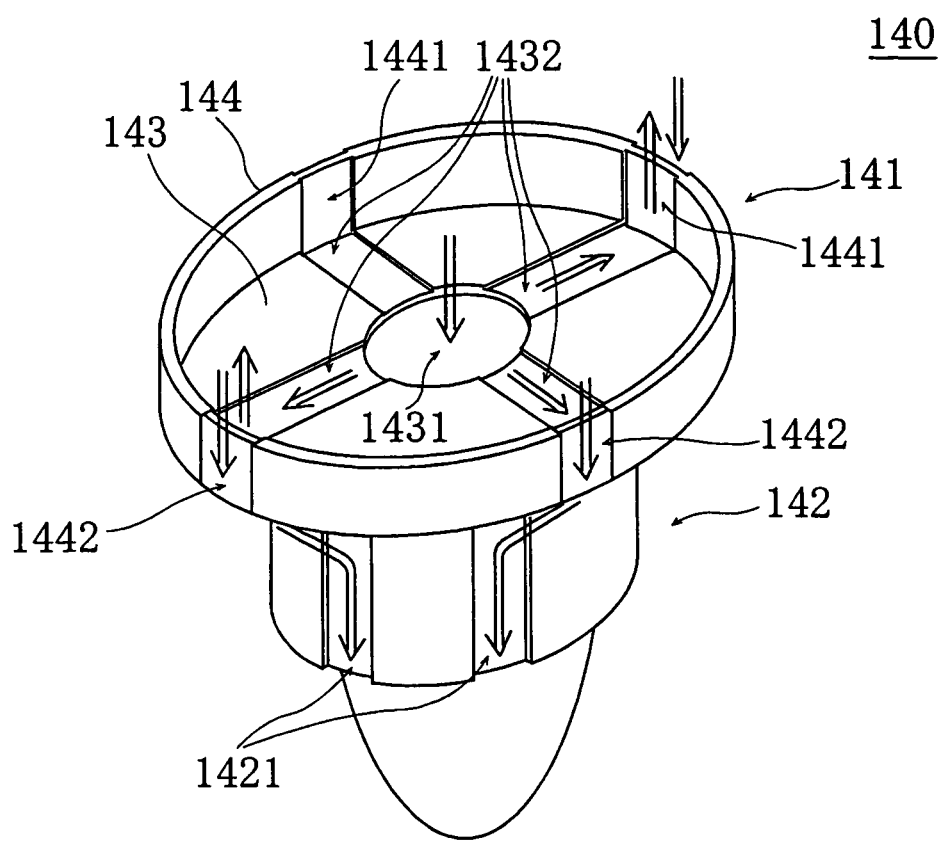
FIG. 5 is a perspective view showing a configuration of a circulating portion 140 of the first embodiment.

FIG. 5 is a perspective view of a circulating portion 140.

As shown in FIG. 5, the circulating portion 140 includes a round plate-shaped circulating-plate portion 141 whose circumferential edge is raised upward and a spindle-shaped holding portion 142 that is projected from the center of the lower surface of the circulating-plate portion.

The circulating-plate portion 141 includes a circular plate portion 143 having substantially the same diameter of that of the inner cavity 114 and an edge portion 144 that is raised upward from the periphery of the circular plate portion.

In the circular plate portion 143, a groove 1431 having a circular shape when viewed from the top is formed in its center, four grooves 1432 radially extending from the groove 1431 to the edge portion 144 are formed, and grooves 1443 (FIG. 4) similar to the grooves 1432 are formed at the positions opposed to the grooves 1432 in the back face of the circular plate portion 143.

In the edge portion 144, grooves 1441 extending from the respective grooves 1432 in the circular plate portions 143 toward the septum 130 are formed on the inner circumferential surface. On the other hand, on the outer circumferential surface of the edge portion 144, grooves 1442 are formed at the positions opposed to the grooves 1441.

The holding portion 142, in which grooves 1421 leading to the grooves 1443 formed on the back face of the circular plate portion 143 are formed extending toward the axis of the leg portion 111 on its circumferential surface, serves to hold the circulating portion 140 inside the inner cavity 114 and serves to regulate a flow of medical fluid guided from the inner cavity 114.

More specifically, as shown in FIG. 3, the holding portion 142 is secured by being engaged forcefully with the narrow tube portion 117 and therefore holds the circulating portion 140 inside the inner cavity 114 while maintaining the state in which the back face of the circular plate portion 143 is in contact with the bottom face of the inner cavity 114. In order to hold the circulating portion 140, the circular plate portion 143 may be engaged forcefully with the inner cavity 114 to be secured thereto. In this case, the holding portion 142 is unnecessary and thus may not be provided, although the effect of regulating a flow is lost.

As shown in FIG. 4, it is preferable that the circulating portion 140 is secured at a position at which when the luer 190 is inserted inside the inner cavity 114 from the septum 130, its top is brought into contact with the circular plate portion 143 and stops, or a position near that top.

By providing the circulating portion 140 at such a position, when a fluid such as a medical liquid is injected from the luer 190 into the inner cavity 114, the fluid hits the groove 1431 shown in FIG. 5 to change its course so that the fluid flows along the grooves 1432 until it hits the edge portion 144. In this case, it is preferable that the maximum width of the groove 1431 is smaller than the maximum width of the luer 190 so as not to prevent the top of the luer 190 from being in contact with the bottom face of the groove 1431 and the fluid from flowing. Next, the fluid that has hit the edge portion 144 changes its course and flows along the grooves 1441 and is flown up to a region 1141 on the septum 130 side in the inner cavity 114 as shown in FIG. 4. In this manner, the circulating portion 140 blocks the flow of the fluid injected from the luer 190 and circulates the fluid to the septum 130 side, so that even if the luer 190 is removed at the end of injection of the fluid, the fluid that has remained in the region 1141 is replaced by a new fluid at the next fluid injection without fail. In other words, in the region 1141 where the fluid conventionally stagnated and was hardly replaced, the fluid is replaced by a new fluid at least at the next fluid injection, and no fluid stagnates continuously.

Here, in the region 1141, stagnation of a medical fluid is problematic especially in a region 1142 (FIG. 4), which is a very small gap surrounded by the back face of the septum 130 that has been deformed by insertion of the luer 190 and the wall face of the inner cavity 114. This very small region 1142 is most away from the exit of the liquid flow of the luer 190 and is a site into which a substitute fluid hardly flows because the deformed septum 130 becomes an obstacle. However, by providing the circulating portion 140 of the present invention, the medical fluid injected from the luer 190 hits the edge portion 144, changes its course so as to flow along the grooves 1441 and is flown up to the small region 1142, which ensures liquid exchange in the region 1142.

The fluid flown up to the regions 1141 and 1142 is bounced back by the septum 130, etc., and drops toward the groove 1442, which is a clearance between the circulating portion 140 and the wall surface of the inner cavity 114, and then passes sequentially through the grooves 1442, 1443, and 1421 to the narrow tube portion 117, and thus eventually infused to a patient (FIG. 4).

Thus, by providing the circulating portion 140, replacement of the fluid that remains in the regions 1141 and 1142 where conventionally the fluid has been hardly replaced can be promoted. The circulating portion 140 has a preferable effect also in the case where the fluid flows from the narrow tube portion 117 side of the channel tube unit 110, for example, in the case where blood is extracorporeally circulated. For example, in the case of extracorporeal circulation, stagnation and coagulation of blood can be prevented by circulating the blood that has been flown in from the narrow tube portion 117 side to the septum 130 side. In this case, the circulating portion 140 serves to circulate the fluid that has been flown in from the narrow tube portion 117 to the septum 130 side, and guide the fluid to the top portion of the luer or the like.

The circulating portion 140 also can position the luer 190 by providing the circulating portion 140 in a position at which the top of the luer 190 is contact therewith. Furthermore, the flow of the fluid injected from the luer 190 is blocked by the circulating portion 140, so that a pressure is applied to the fluid and the speed of the fluid flowing the grooves and the internal portion of the inner cavity 114 can be increased.

Therefore, it is believed that the replacement efficiency can be improved from conventional devices and the growth of microorganisms such as bacteria can be suppressed. Thus, when the mixture injection port of the present invention is used by outpatients who control their central venous catheters, which conventionally could not be recommended, infections through the catheter can be suppressed.

Such a circulating portion 140 can be used with a conventional mixture injection port, if it is produced in a shape that is in accordance with the conventional mixture injection port, and therefore this is cost-efficient.

Furthermore, in the above-described embodiment, an extension tube is inserted on the leg portion 111 side and fixed, but there is no particular limitation regarding the fixing method. For example, also when a known female luer lock connector is fixed to the structure of that portion, the same effect as in this embodiment can be obtained.

In the above-described embodiment, a medical liquid is injected with a luer, but the present invention is not limited thereto, and a cannula is used to flow a cleaning liquid after injection or blood collection.

Second Embodiment

In the first embodiment, grooves are formed in a circulating-plate portion in the circulating portion. However, in the second embodiment, the portion in which the grooves are formed and the other portions are reversed. In other words, ribs are formed in the portion in which the grooves were formed, so that a medical fluid can flow between the ribs. The mixture injection port of the second embodiment is different from the mixture injection port of the first embodiment only in the configuration of the circulating portion 140, and therefore different aspects from those in the first embodiment will be primarily described in the following.

Figure 6:
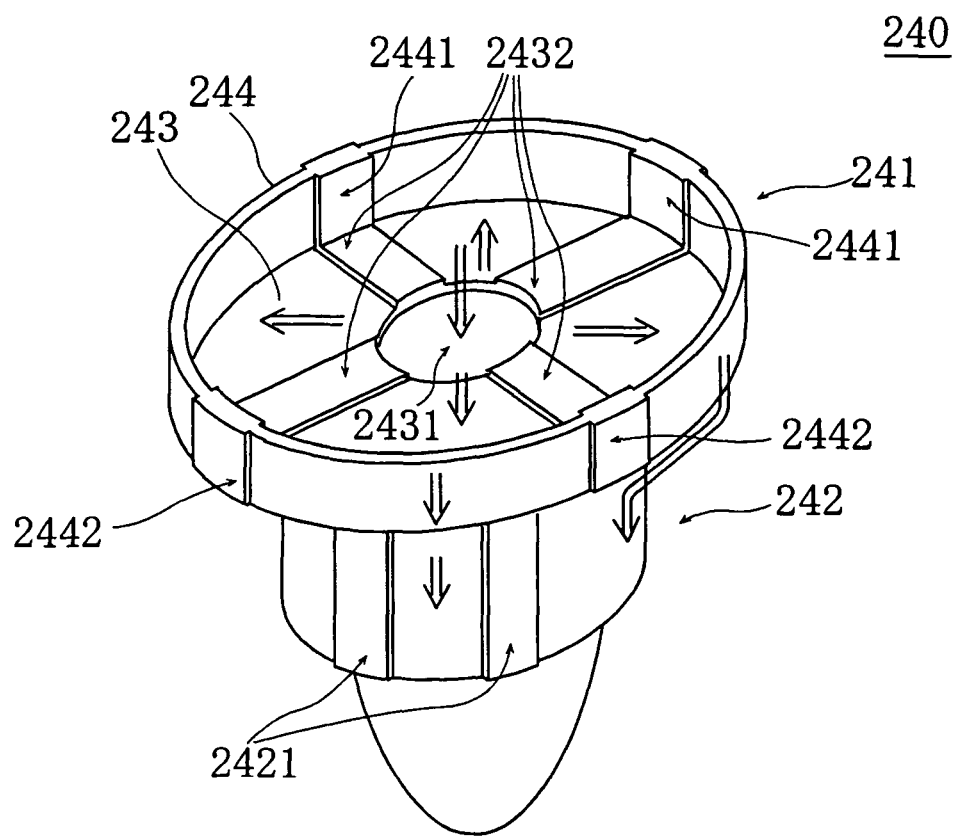
FIG. 6 is a perspective view showing a configuration of a circulating portion 240 of the second embodiment.

FIG. 6 is a perspective view of a circulating portion 240 of the second embodiment.

As shown in FIG. 6, the circulating portion 240 includes a circulating-plate portion 241 and a holding portion 242 that is projected from the center of the lower surface of the circulating-plate portion, as in the first embodiment, and serves to suppress the stagnation in the regions 1141 and 1142 (FIG. 4) in the inner cavity 114 of the mixture injection port.

The circulating-plate portion 241 includes a circular plate portion 243 having substantially the same diameter of that of the inner cavity 114 and an edge portion 244 that is raised upward from the edge portion of the circular plate portion.

Herein, in the circular plate portion 243 and the edge portion 244 of the circulating-plate portion 241 and the holding portion 242, ribs 2432, 2441, 2442, 2443 (not shown), and 2421 are formed in the portion where the grooves 1432, 1441, 1442, 1443 and 1421 are formed in FIG. 5 in the first embodiment. Thus, wider grooves than in the first embodiment are formed between the ribs and the channel resistance for a medical fluid can be reduced. Therefore, it is believed that a medical fluid can be injected more smoothly than in the first embodiment while suppressing the stagnation of the medical fluid.

Application Example

One example in which the mixture injection ports of the first and the second embodiments are applied in practice in the medical field will be described. The mixture injection ports of the third and the fourth embodiments, which will be described later, also can be applied to this application example in the same manner.

For example, when infusing a liquid to a patient, an extension tube is connected to a central venous catheter that is placed in an artery of the patient, and the mixture injection port is connected to the extension tube. The mixture injection port is used in the state where a luer connected to an infusion solution set from an infusion solution bag that is filled with a fat emulsion, a glucide transfusion, an amino acid transfusion or the like is inserted on its septum side. In this case, the infusion solution set is exchanged, for example, every one to four days.

When the mixture injection port is used in this manner, continuous stagnation of a liquid in the inner cavity can be suppressed, so that even if some microorganisms such as bacteria enter the port, the microorganisms are not grown and are flown out together with the infusion liquid. Thus, it is possible to suppress growth of microorganisms such as bacteria in the mixture injection. In such a use method, when a conventional mixture injection port is used, microorganisms such as bacteria are grown in a stagnation portion in the inner cavity and the grown microorganisms enter the body.

When collecting blood from a patient, an extension tube is connected to a central venous catheter that is placed in an artery of the patient, and the mixture injection port of the present invention is connected to the extension tube. A luer for collecting blood is inserted into a slit of the septum in the mixture injection port and the blood is collected, and then the luer is removed. Thereafter, in order to prevent microorganisms such as bacteria from growing in the blood that has remained in the inner cavity of the mixture injection port and to prevent the blood that has remained from coagulating, a luer is inserted into the slit of the septum again and heparin is injected therethrough to flush-clean the inner cavity.

In the conventional mixture injection port, a region in which a medical fluid is hardly replaced is formed in the inner cavity, so that the remaining blood cannot be cleared, and therefore it is possible that microorganisms such as bacteria grow. However, using the mixture injection port of the present invention, the inner cavity can be sufficiently cleaned and continuous stagnation of blood can be suppressed, so that growth of microorganisms such as bacteria can be suppressed.

Embodiment 3

Next, a third embodiment of the present invention will be described.

Figure 7:
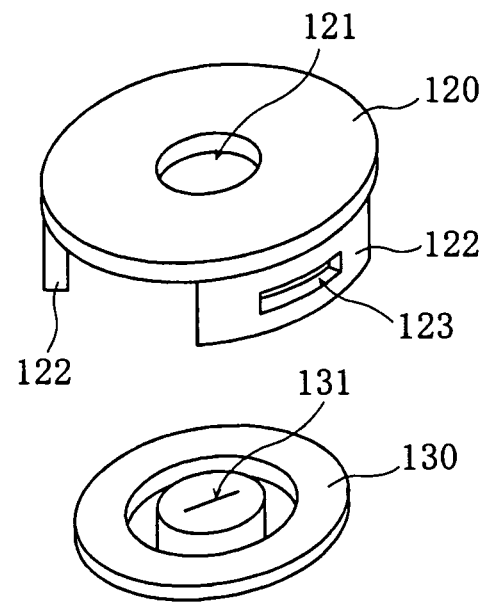
FIG. 7 is an exploded perspective view for illustrating an example of configuration of a mixture injection port of a third embodiment of the present invention.
Figure 7:
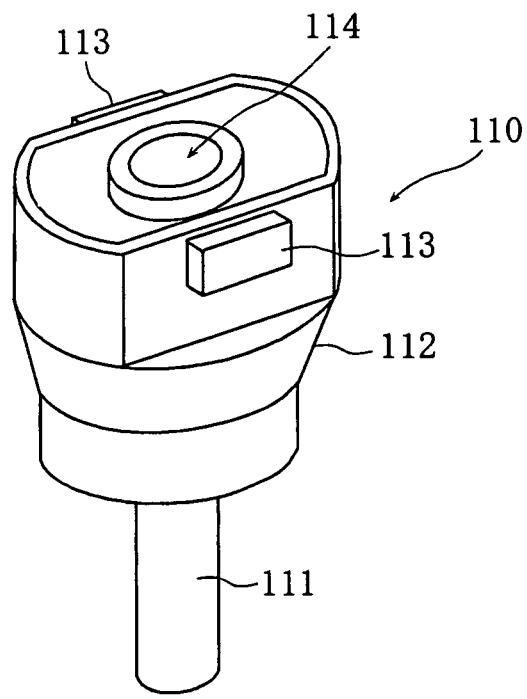
Figure 8:
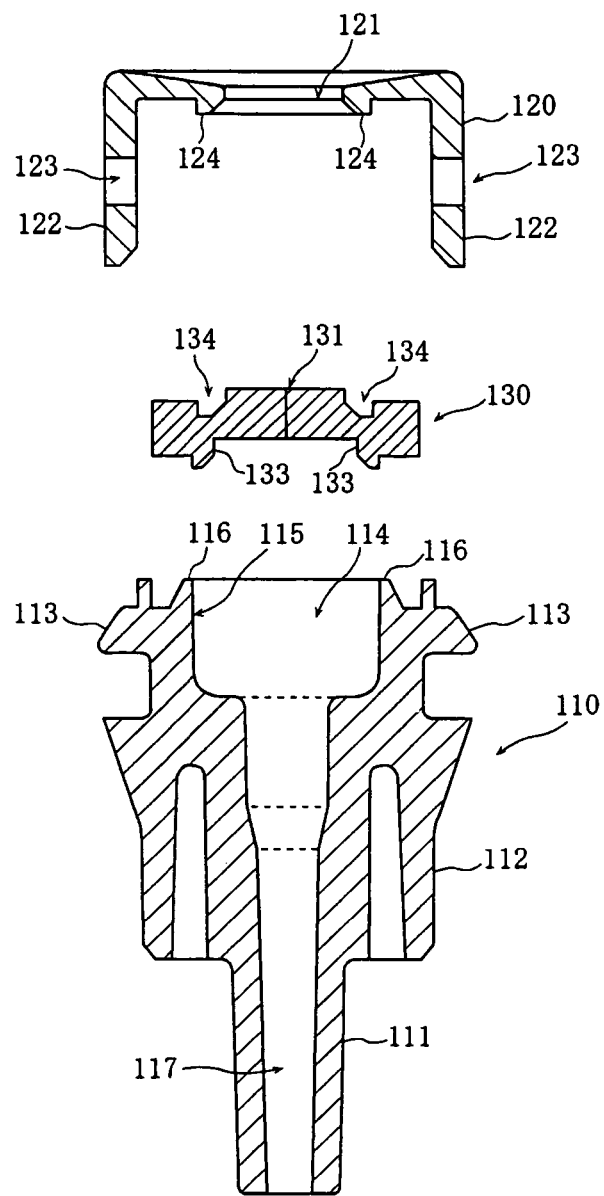
FIG. 8 is a cross-sectional view of each portion shown in FIG. 7.

FIG. 7 is an exploded perspective view for illustrating a configuration of a mixture injection port 100 of this embodiment. FIG. 8 is a cross-sectional view of each portion shown in FIG. 7. As shown in FIGS. 7 and 8, the mixture injection port 100 of this embodiment includes a channel tube unit 110, a cap unit 120 and a septum 130. The channel tube unit 110 and the cap unit 120 have been described in the first embodiment and therefore will not be described in detail herein. This embodiment is different from the first embodiment in that an annular rib 133 is provided on the inner cavity 114 side of the septum 130.

Figure 9:
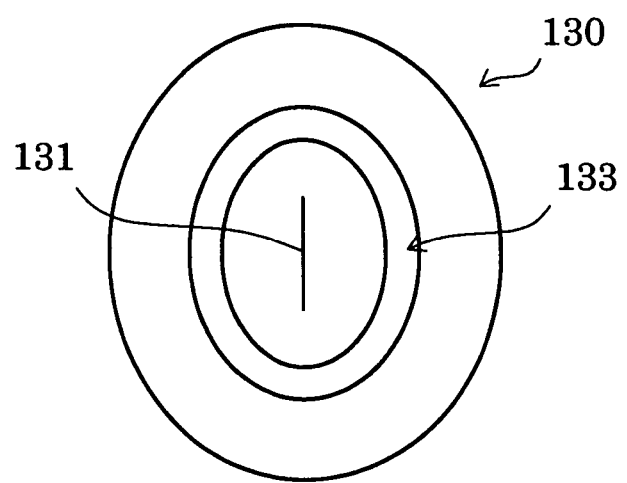
FIG. 9 is a bottom view of a septum 130 of the third embodiment viewed from the inner cavity 114 side.

More specifically, an engaging hole 123 provided in each of a pair of engaging portions 122 of the cap unit 120 is engaged with an engaging protrusion 113, and when the septum 130 is latched with the channel tube unit 110 while being pressed thereto, the outer edge 116 of the inner cavity 114 is attached to the outer circumference of the annular rib 133 provided as a fluid-stagnation-preventing portion in the septum 130 without any gap in this embodiment. FIG. 9 is a bottom view of the septum 130 viewed from the channel rube portion 110 side.

An insertion hole 121 is provided in the center of a disk-shaped member in an upper portion of the cap unit 120, and an annular septum fixing portion 124 provided in the outer circumference of the insertion hole 121 is attached to an annular groove portion 134 provided in an upper portion of the septum 130, so that the insertion hole 121 is fixed to the septum 130 so as to be covered thereby while the positional relationship between the slit 131 and the insertion hole 121 is fixed. This embodiment is the same as the first embodiment in that the septum 130 is formed by shaping an elastic material such as isoprene rubber and silicon rubber, and that the slit 131 is formed in the center thereof, and the annular rib 133 is formed integrally with the septum 130.

The slit 131 is usually closed while being pressed by the elasticity of the septum 130, but when a tube member such as a luer is inserted therein, the septum 130 near the slit 131 is deformed to the insertion direction (in the direction toward the inner cavity 114), and the inner cavity 114 becomes open while retaining a substantially air-tight state. In this embodiment, the outer circumference of the annular rib 133 is in contact with the inner wall 115 of the inner cavity 114, which is substantially elliptical, throughout its entire circumference. Thus, the sealing performance of the inner cavity 114 at the time of inserting and removing the tube member can be increased.

The size of the insertion hole 121 can be designed in accordance with the application or the size of a member such as a luer and a cannula that is to be inserted. In this embodiment, the inner diameter is about 3.8 to 5.5 mm, and the inner diameter of the inner cavity 114 is about 4.5 to 8.5 mm. The lower limit of the inner diameter of the inner cavity 114 can be designed so as to ensure a space that can accommodate deformation of the septum 130 when a luer or the like is inserted. On the other hand, the upper limit can be designed so as to prevent a gap portion in which a medical fluid can remain at the deformation of the septum 130 from occurring.

The thickness (portion in which the slit 131 is formed) of the septum 130 is about 0.5 mm to 4.0 mm. When it is less than 0.5 mm, there may be problems in the sealing performance and the pressure resistance of the slit, and when it is more than 4.0 mm, the resistance to the insertion of the luer or the like becomes large. These values can be optimized, depending on whether it is a luer or a cannula that is to be inserted or what is the size thereof.

As described above, in the mixture injection port 100 of this embodiment, the annular rib 133 is provide in a lower portion (inner cavity 114 side) of the septum 130 as a fluid-stagnation-preventing portion that suppresses generation of a gap portion (regions 1141, 1142 shown in FIG. 4 in the first embodiment, which are collectively referred to as "gap region") in which a fluid such as an infusion liquid and blood may remain between the septum 130 and the inner wall 115 of the inner cavity 114 when a luer or the like is inserted into the slit 131.

Figure 10:
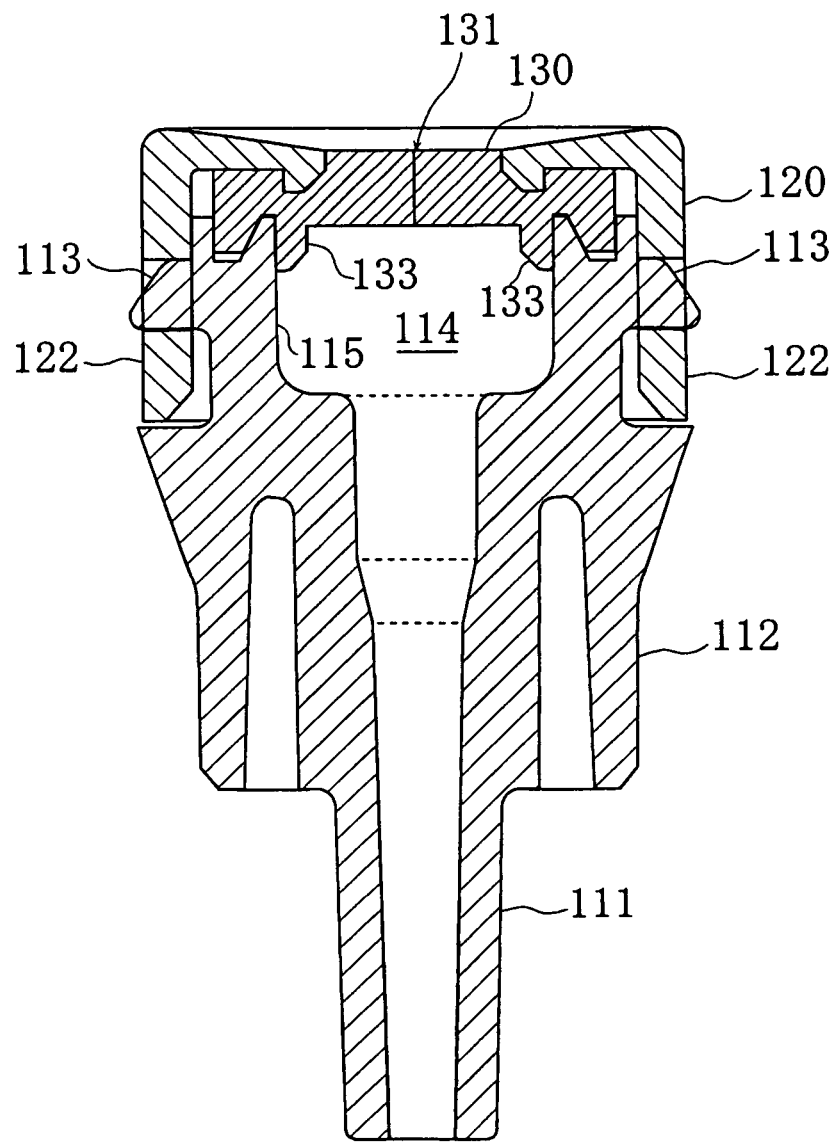
FIG. 10 is a cross-sectional view of the mixture injection port of the third embodiment.
Figure 11:
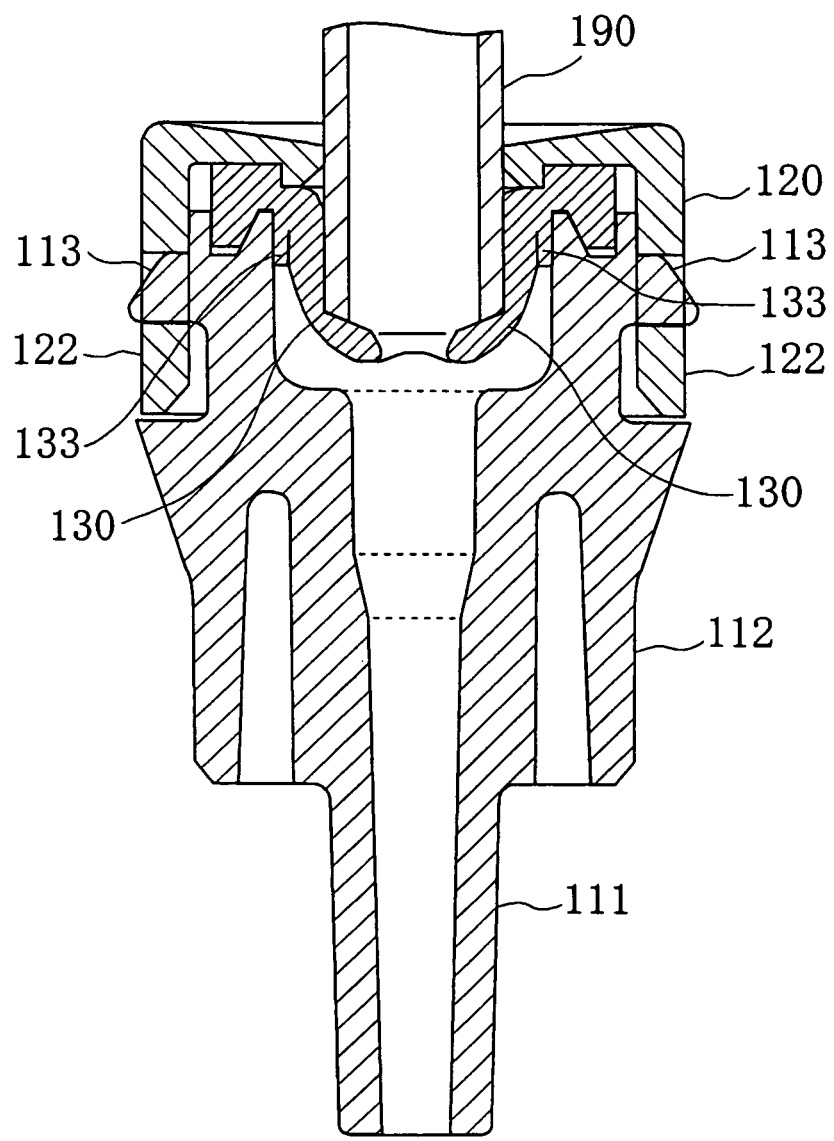
FIG. 11 is a cross-sectional view showing a state in which a luer 190 is inserted into a slit 131.

Hereinafter, suppression of generation of the gap region by providing such an annular rib 133 will be described. FIG. 10 is a cross-sectional view of the mixture injection port 100 that is assembled. FIG. 11 is a cross-sectional view showing a state in which a luer 190 is inserted into the slit 131 in the mixture injection port 100.

As shown in FIG. 11, when the luer 190 is inserted into the slit 131 and the septum 130 is deformed to the inner cavity 114 side, the annular rib 133 serves to fill the gap region between the deformed septum 130 and the inner wall 115 of the inner cavity 114. Therefore, the infusion liquid or blood that remains in the gap portion when the annular rib 133 is not provided is prevented from remaining, and more efficient internal cleaning can be achieved at flush cleaning with a detergent.

As shown in the bottom view of FIG. 9, the outer circumstance of the annular rib 133 is in contact with the inner wall 115 throughout the entire circumference of the inner cavity 114, and thus generation of the gap region between the inner wall 115 of the inner cavity 114 and the septum 130 is suppressed, and the sealing performance of the inner cavity 114 can be increased. Furthermore, the annular rib 133 is formed integrally with the septum 130, and the annular rib 133 is made of an elastic material such as isoprene, so that when a luer or the like is inserted, the elasticity of the annular rib 133 presses the septum 130 to the side of the luer and therefore the sealing performance between the luer and the septum 130 and the fixing performance of the luer or the like can be improved.

Figure 12:
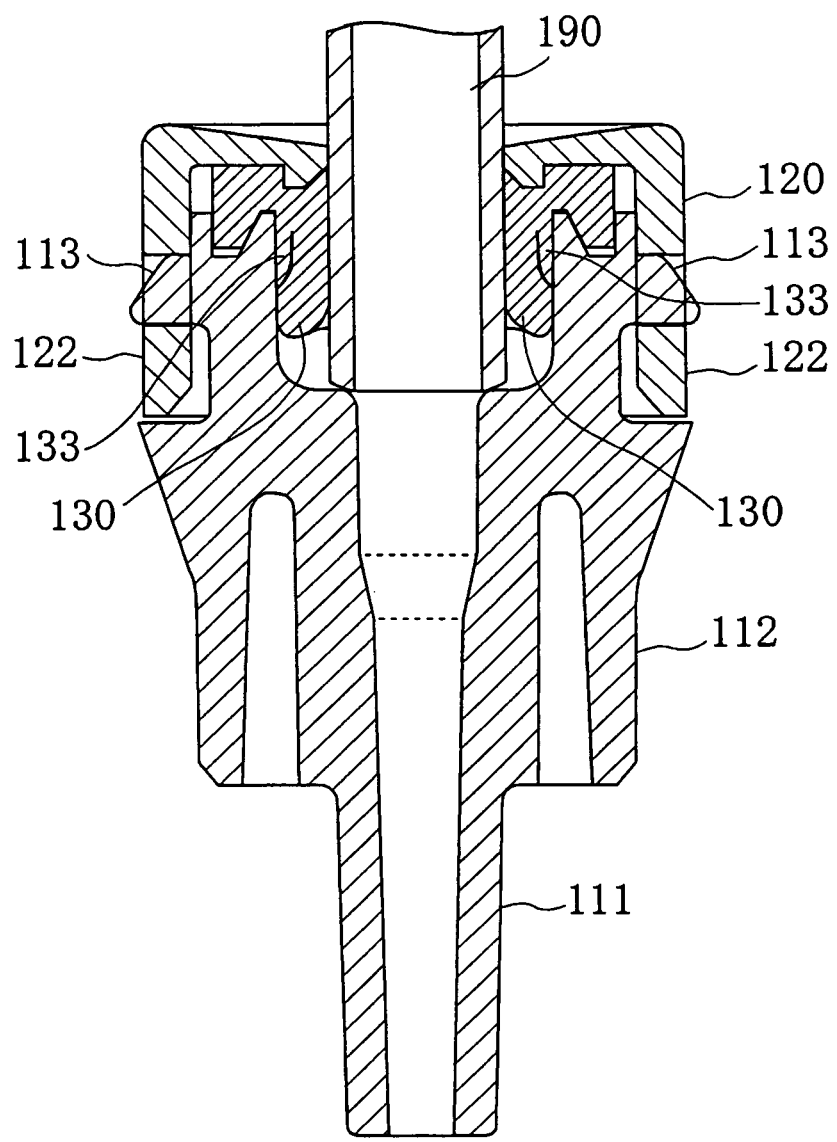
FIG. 12 is a cross-sectional view showing a state in which a luer 190 is inserted deeply in a slit 131.

The width and the height of the annular rib 133 are each about less than 3.0 mm in this embodiment. This is, for example, because when the width of the annular rib 133 is too large, this may cause a resistance when a luer is inserted. When the height is limited to less than 3.0 mm, when a luer is inserted deep, the septum 130 can be fit below the annular rib 133, that is to say, a space to which the septum 130 can be fit can be obtained (see FIG. 12). The width and the height of the annular rib 133 can be optimized, depending on the purpose of use, the size of the entire mixture injection port 100, the kind of the tube member such as a luer or the like.

Embodiment 4

Next, a fourth embodiment of the present invention will be described. In this embodiment, the circulating portion 140 that is described in the first embodiment is provided, and the annular rib 133 is provided. The circulating portion 140 has been described in detail in the first and the second embodiments, and therefore the circulating portion itself will not be described herein.

Figure 13:
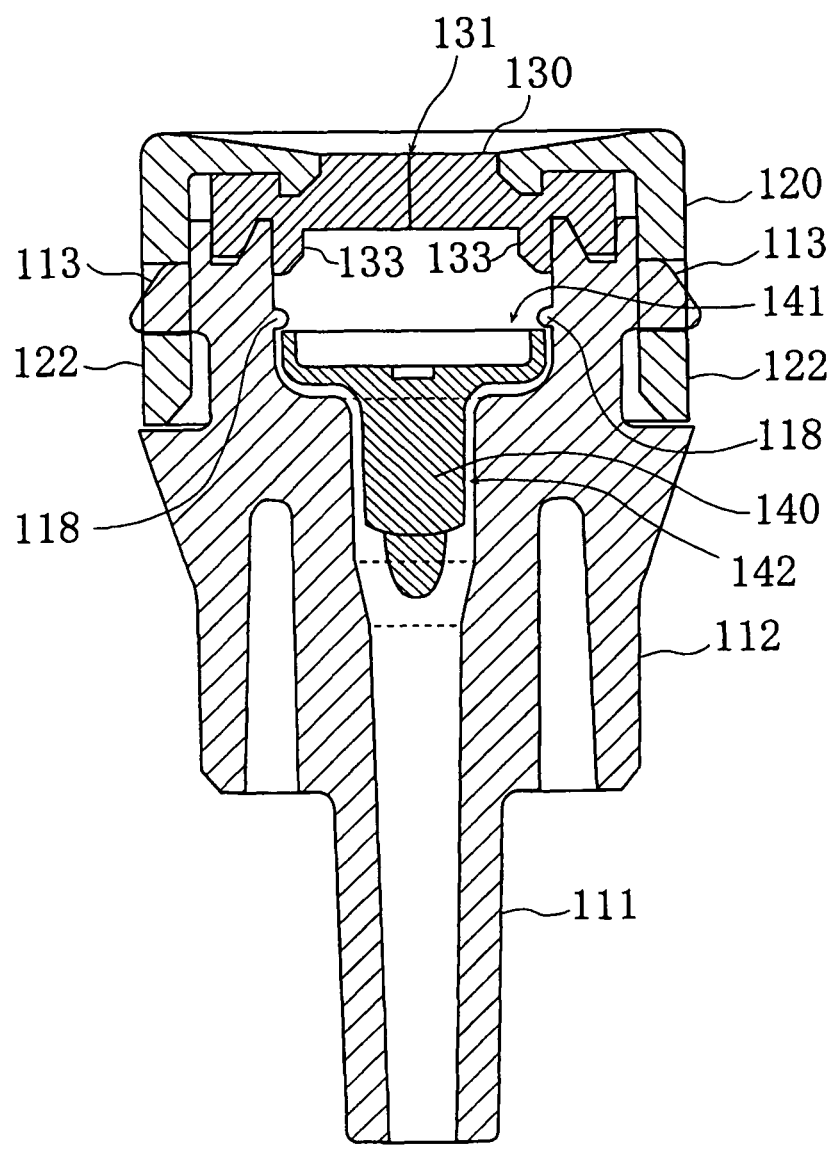
FIG. 13 is a cross-sectional view of a mixture injection port of a fourth embodiment.

FIG. 13 is a cross-sectional view of a mixture injection port of this embodiment. This embodiment is the same as what is described in the first embodiment (see FIG. 3) except that the annular rib 133 is provided in the inner cavity 114 side of the septum 130.

Figure 14:
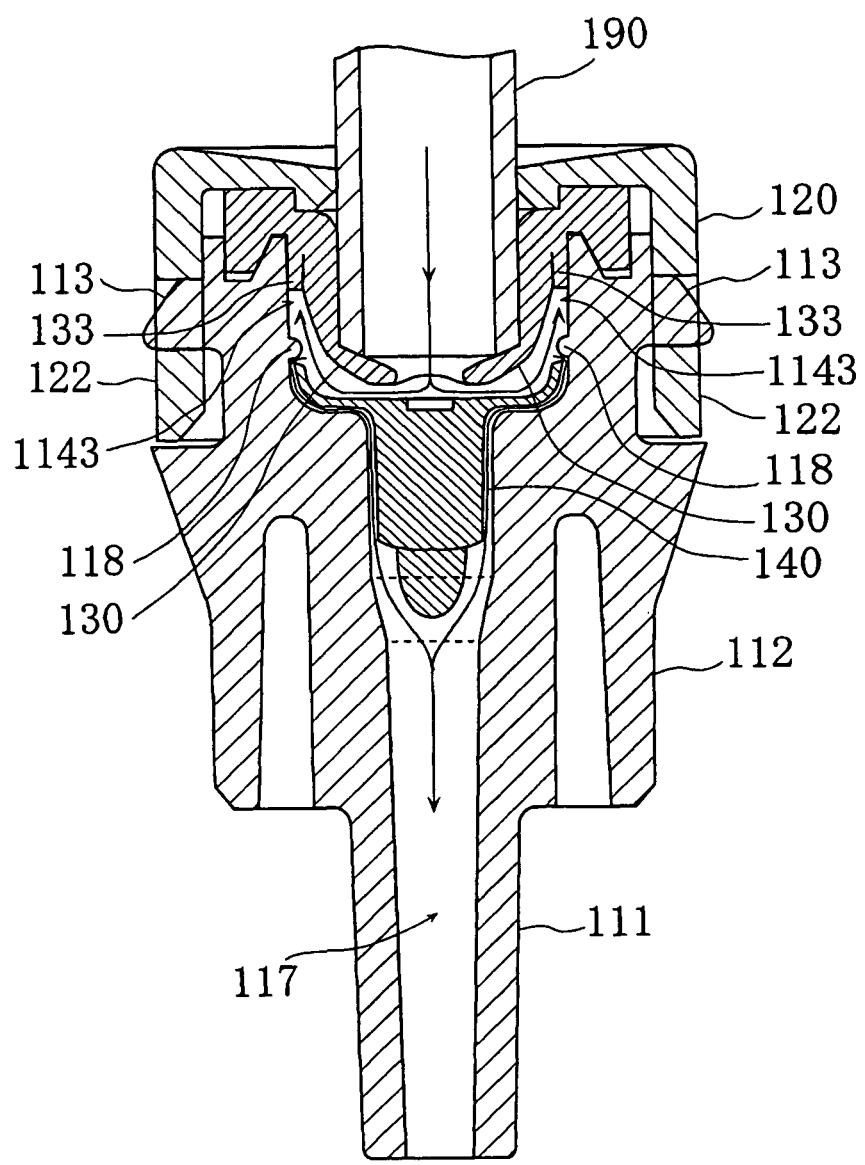
FIG. 14 is a cross-sectional view for illustrating the function of the circulating portion 140 in the fourth embodiment.

Hereinafter, the function of the circulating portion 140 in this embodiment will be described. FIG. 14 is a cross-sectional view for illustrating the function of the circulating portion 140.

The function of the circulating portion 140 in this embodiment is basically the same as described in the first and the second embodiments. In particular, when the inside of a connecter is flush-cleaned with a detergent, the circulating portion 140 blocks a flow of the detergent such as heparin or a physiological saline solution that has flown rapidly in the inner cavity 114 to circulate the flow to the septum 130 side and guides the flow to the region 1143 that is formed of the septum 130, the annular rib 133 and the inner wall 115 (the direction in which the injected detergent flows is shown in FIG. 14). In this region 1143, the gap region 1141, etc. that has been described, for example, in the first embodiment is filled by the function of the annular rib 133.

This function of the circulating portion 140 together with the function of the annular rib 133 makes it possible to clear and remove the fluid such as infusion liquid that remains between the septum 130 and the inner wall 115 more efficiently, and even if infusion is suspended for a long time, growth of microorganisms or the like in the inside of the connector can be prevented more reliably.

FIG. 15 is a table showing the results of tests regarding the effect when the circulating portion 140 is provided and an annular rib 133 is provided in the septum 130, as in this embodiment. The example of FIG. 15 shows the amount of the remaining liquid (average of three tests) when the inner cavity 114 is filled with bovine blood or fat emulsion, and then a flush-cleaning treatment is performed with a physiological saline solution. The amount of remaining bovine blood was determined by measuring the concentration of hemoglobin, and the amount of remaining fat emulsion was determined by measuring light transmittance of the remaining liquid. As shown in FIG. 15, the effect of preventing a fluid from remaining in the case where the annular rib 133, in addition to the circulating portion 140, is provided is evidently exhibited.

The configuration of the circulating portion 140 is not limited to those described in the embodiments described above.

For example, although in the first embodiment, four grooves extending from the groove 1431 are formed, the number of the grooves is not limited to four, and at least one groove is sufficient. There is no limitation regarding the position for formation.

In the embodiments described above, the edge portion 144 is provided in a circular shape. However, when the slit 131 of the septum 130 has a shape of a straight line, as in the above-described embodiments, the gap region (1141, 1142 in FIG. 4) is formed in parallel to the slit 131, so that the edge portion 144 may be provided only in a necessary portion to circulate a medical fluid to the regions 1141 and 1142.

Furthermore, in the circulating portion 140, the groove 1441 is formed in the edge portion 144. However, the fluid can be flown up to the region 1141 by the edge portion 144 without the groove 1441, so that it is not necessary to form the groove.

If the portion in which the edge portion 144 rises up from the circular plate portion 143 is rounded, or the edge portion 144 is inclined outwardly, the boundary region between the septum 130 and the inner wall 115 can be cleaned, so that doing so is more preferable. Furthermore, in order to prevent a fluid from remaining on the circulating portion 140, for example, a narrow channel through which a fluid can flow from the central portion of the groove 1431 to the narrow tube portion 117 formed in the leg portion 111 may be formed.

Application Example

An example of an infusion method when the mixture injection ports of the third and the fourth embodiments are applied in practice in the medical field for infusion will be described. The mixture injection ports of the first and the second embodiments also can be applied to this application example. For example, when central venous nutrition is performed to a patient with the mixture injection port of the present invention, an extension tube is connected to a central venous catheter that is placed in a vein of the patient, and the extension tube is connected to the leg portion 111 of the connector of the present invention. For central venous nutrition, intermittent injection may be performed in order to treat a patient at home or allow a patient to return to normal life. In this therapy, a necessary amount of infusion liquid per day is administered for 8 to 12 hours, and the infusion is suspended in the remaining hours. At the suspension of the infusion, heparin, a physiological saline solution or the like is flushed. When flushing is insufficient because of stagnation, the risk of infection due to growth of microorganisms is increased.

When collecting blood from a patient, an extension tube is connected to a central venous catheter that is placed in a vein of the patient, and the extension tube is connected to the leg portion 111 of the connector of the present invention. The connector is used with a luer for collecting blood being inserted into a slit 131 formed in the septum, and the luer is removed after blood is collected. Thereafter, in order to prevent the collected blood from coagulating in the inner cavity 114, a luer is inserted into the slit 131 again and heparin or the like is flushed for cleaning the inner cavity 114. As described in the above embodiments, when the connector of the present invention is used, the inner cavity can be cleaned efficiently by the flush-cleaning treatment, and the fluid such as a liquid for intravenous hyperalimentation or blood can be prevented from staying, so that growth of microorganisms especially in the gap portion between the septum and the inner wall of the inner cavity 114 can be prevented more reliably. The above-described application example and the application examples described in the first and the second embodiments can be used effectively for animals other than human beings.

Embodiment 5

Next, a fifth embodiment of the present invention will be described. Also in this embodiment, the shape of the septum 130 is changed. Hereinafter, the aspects that already have been described in the above embodiments are omitted and different aspects from above will be described.

Figure 16:
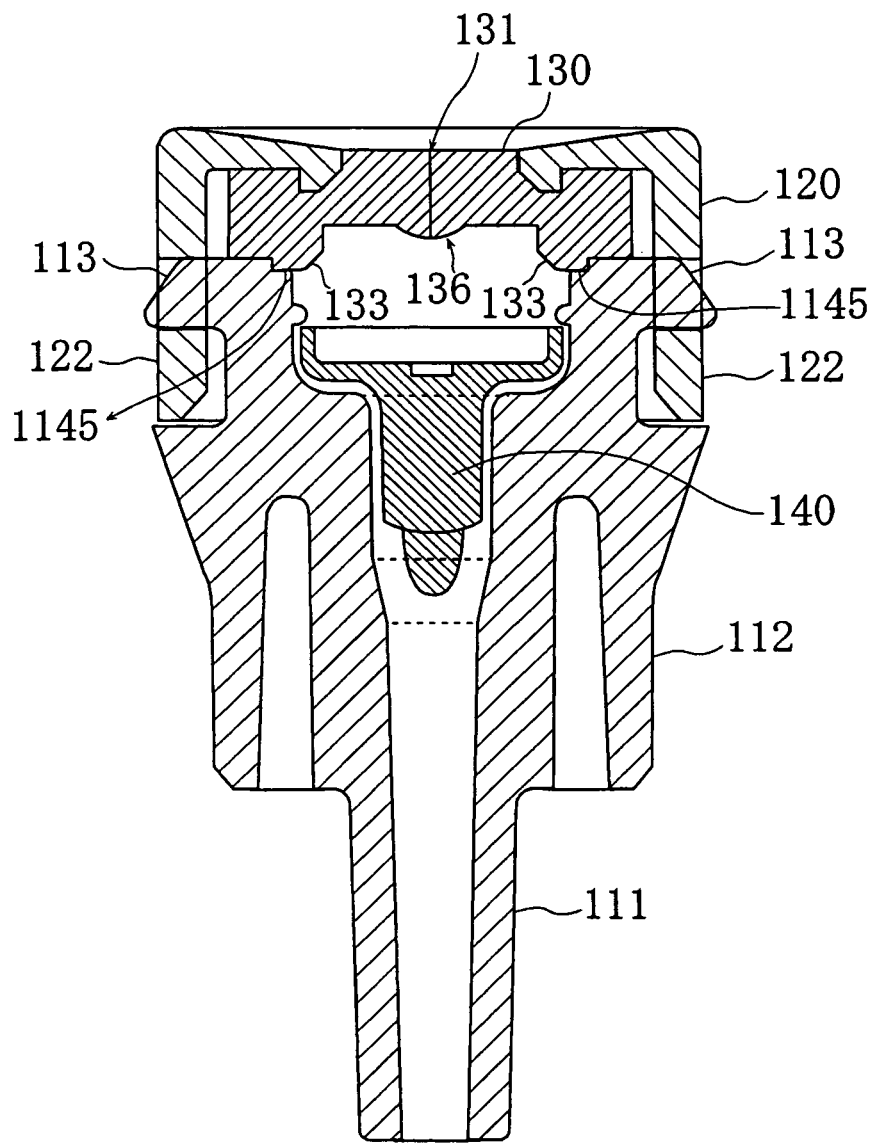
FIG. 16 is a cross-sectional view of a mixture injection port of a fifth embodiment.

FIG. 16 is a cross-sectional view of a mixture injection port of this embodiment and is different from what is described in the fourth embodiment (see FIG. 13) in that a septum 130 having a different shape is used as the septum 130. The shape of the septum 130 is simplified, and the shape of the inner cavity 114 in the channel tube unit 110 is also different, that is, a step 1145 that is tightly in contact with the edge of the annular rib 133 is provided in the inner wall portion of the inner cavity 114.

In the mixture injection port of this embodiment, the shapes of the channel tube unit 110 and the septum 130 are simplified, and the process of engaging the outer circumference of the annular rib 133 formed in the septum 130 and the outer edge 116 of the inner cavity 114 formed in the channel tube unit 110 without any gap, as in the above embodiments (e.g., see FIG. 8), can be eliminated, so that a mixture injection port that can be produced more easily can be provided.

In the mixture injection port of this embodiment, the thickness of the annular rib 133 is large, and when the face of the slit on the inner cavity side is flat and the septum 130 is fixed to the channel tube unit 110 with the cap unit 120, the slit 131 may be slightly open on the surface side. Therefore, in this embodiment, this problem is prevented by forming a protrusion 136 integrally with the back surface (periphery of the slit 131) of the septum 130.

Variation Example

The embodiments of the present invention have been described above, but the present invention is not limited to the specific examples described in the above embodiments, and for example, the following variation examples can be encompassed.

Figure 17:
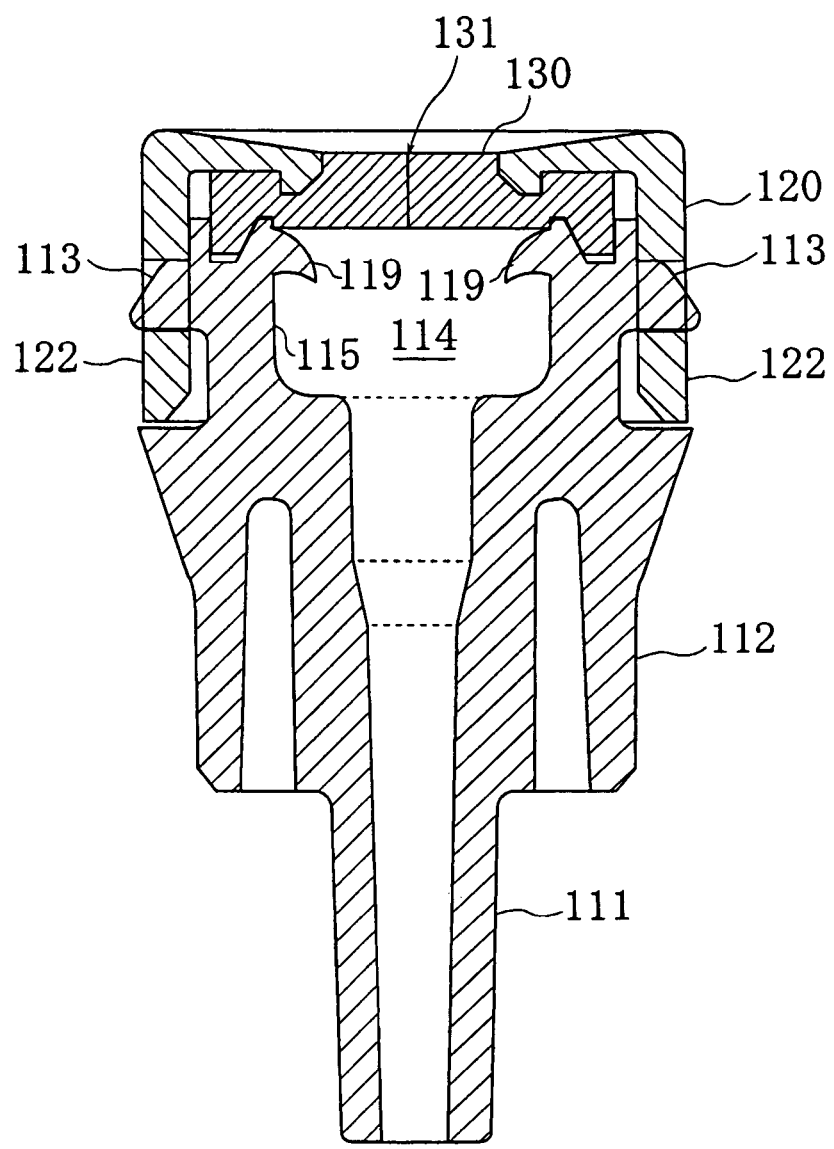
FIG. 17 is a cross-sectional view showing an example when a portion that is projected from the inner wall 115 side is provided as a fluid-stagnation-preventing portion.

(1) In the third embodiment, the annular rib 133 is formed integrally with the septum 130 on the inner cavity 114 side of the septum 130, so that the gap region in which the fluid remains can be suppressed from being generated. This method has advantages in that the number of member is not increased, so that assembling is simple and the mixture injection port can be achieved at low cost. However, the method of preventing generation of the gap region is not limited thereto, and it is possible to prevent generation of a portion in which a fluid remains, for example, by providing a fluid-stagnation-preventing portion 119 that protrudes from the inner wall 115, as shown in FIG. 17. The shape of the fluid-stagnation-preventing portion 119 is not limited to the shape shown in FIG. 17, and its shape can be semi-spherical, or wedge-shaped or in other shapes.

(2) In the above embodiments, the case where the septum 130 is penetrated by the slit 131 from the beginning, as shown in the cross-sectional view of FIG. 3, has been described, but the septum 130 does not necessarily have to be penetrated by the slit 131 from the beginning, and a configuration in which when a luer or the like at the first time is inserted, the septum 130 is completely penetrated can be encompassed.

Figure 18:
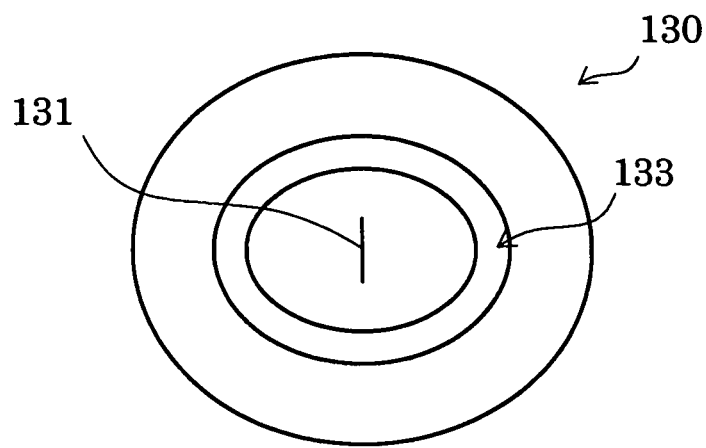
FIG. 18 is a bottom view of the septum 130 when the slit 131 is provided in the direction along the minor axis of the septum 130.

(3) In the above embodiments, the case where the slit 131 is provided along the direction of the major axis of the substantially elliptical septum 130 has been described, but especially when the septum 130 is elliptical, it is preferable that the slit 131 is provided along the direction of the minor axis of the septum 130, as shown in the bottom view of FIG. 18, in order to increase the sealing performance of the inner cavity 114 when a tube member such as a luer is inserted into the slit 131.

INDUSTRIAL APPLICABILITY

The present invention can be applied to a mixture injection port used, for example, for intravenous nutrition, blood transfusion, blood collection or the like.

The invention claimed is:

1. A mixture injection port comprising:
a channel tube unit including a body portion that is provided with an inner cavity and a leg portion that is provided with a narrow tube portion having a smaller width than that of the inner cavity;
a septum covering one end of the channel tube unit and having a slit into which a tube member is inserted; and
a circulating member provided in the channel tube unit below the septum, the circulating member being separate from the channel tube unit and comprising:
   a plate portion arranged to change direction of flow of a first fluid injected from the inserted tube member or a second fluid flowing from the other end of the channel tube unit; and
   an edge portion that protrudes upwardly towards the septum from a periphery of the plate portion and is arranged along an inner wall of the channel tube unit,
wherein the circulating member is positioned such that a tip of the edge portion faces a gap region between the inner wall of the channel tube unit and the septum deformed by the insertion of the tube member,
wherein the circulating member is configured to: circulate the first fluid injected from the inserted tube member to the gap region such that at least a portion of a surface of the septum is in contact with at least a portion of the circulating first fluid redirected by the circulating plate portion to substantially flush away any stagnant matter present on said surface of the septum and then guide the first fluid to the other end of the channel tube unit, and/or circulate the second fluid flowing from the other end of the channel tube unit to the gap region and then guide the second fluid to a top portion of the inserted tube member,
wherein an axial position of the circulating member in the channel tube unit is substantially restricted when the tube member is inserted into or pulled out of the slit; and
wherein an annular protrusion is formed on the inner cavity of the channel tube such that the plate portion of the circulating member is engaged between the annular protrusion and a step formed between the inner cavity and the narrow tube portion such that an axial position of the circulating member in the channel tube unit is substantially restricted when the tube member is inserted into or pulled out of the slit.

2. The mixture injection port according to claim 1, wherein the narrow tube portion is configured to provide communication between the inner cavity and the other end of the channel tube.

3. The mixture injection port according to claim 2, wherein a groove is formed on a surface on the inner cavity side of the plate portion of the circulating member, the groove extending in a direction different from a direction from which the first fluid is injected from the inserted tube member, and wherein the first fluid is allowed to flow along the groove so that the direction of flow of the first fluid is changed.

4. The mixture injection port according to claim 2, wherein the plate portion of the circulating member is provided with a holding portion on its back face that is engaged with the narrow tube portion and holds the circulating member inside the channel tube.

5. The mixture injection port according to claim 4, wherein a groove for guiding the first fluid or the second fluid is formed in the back face of the plate portion and the holding portion.

6. The mixture injection port according to claim 1, wherein a groove for guiding the first fluid or the second fluid is formed on an inner circumferential surface and an outer circumferential surface of the edge portion.

7. The mixture injection port according to claim 1, further comprising:
a fluid-stagnation-preventing portion provided for filling the gap region generated between the inner wall of an inner cavity formed inside the channel tube and the septum that is deformed to the inner cavity side by insertion of the tube member, when the tube member is inserted into the slit.

8. The mixture injection port according to claim 7, wherein the fluid-stagnation-preventing portion is formed integrally with the septum.

9. The mixture injection port according to claim 8, wherein the fluid-stagnation-preventing portion is a rib provided such that at least one portion of its outer circumference and its top is in contact with the inner wall throughout its entire circumference.

10. The mixture injection port according to claim 7, wherein the fluid-stagnation-preventing portion is provided so as to protrude from the inner wall and be in contact with the septum.

11. A mixture injection port comprising:
a channel tube unit including a body portion that is provided with an inner cavity and a leg portion that is provided with a narrow tube portion having a smaller width than that of the inner cavity;
a septum covering one end of the channel tube unit and having a slit into which a tube member is inserted; and
a circulating member provided in an inner cavity of the channel tube unit below the septum, the circulating member being separate from the channel tube unit and comprising:
   a plate portion arranged to change direction of flow of a first fluid injected from the inserted tube member or a second fluid flowing from the other end of the channel tube unit; and
   an edge portion that protrudes upwardly towards the septum from a periphery of the plate portion and is arranged along an inner wall of the channel tube unit,
wherein the circulating member is positioned such that a tip of the edge portion faces a gap region between the inner wall of the channel tube unit and the septum deformed by the insertion of the tube member,
wherein the edge portion is configured to further change the direction of flow of the first fluid or the second fluid towards the gap region such that at least a portion of a surface of the septum is in contact with at least a portion of the circulating first fluid redirected by the circulating plate portion to substantially flush away any stagnant matter present on said surface of the septum, and
wherein an axial position of the circulating member in the channel tube unit is substantially restricted when the tube member is inserted into or pulled out of the slit, the circulating member is positioned at a step formed between the inner cavity and the narrow tube portion.

12. The mixture injection port according to claim 11, wherein a first groove is formed on a surface of the plate portion of the circulating member and the first fluid flows along the first groove towards the edge portion; and
a second groove is formed on a surface of the edge portion of the circulating member and the first fluid flows along the second groove towards the septum side.

13. The mixture injection port according to claim 11, wherein
  the channel tube unit forming a fluid channel in which an inner cavity and the narrow tube portion having a smaller width than that of the inner cavity are in communication with each other;
  the septum covers an opening on the inner cavity side of the channel tube unit;
  the plate portion of the circulating member is mounted on the step between the inner cavity and the narrow tube portion; and
  the annular rib is provided such that its outer circumference side or its top is in contact with an inner wall of the inner cavity is provided in the septum on the inner cavity side by integral formation with the septum,
  and further comprising: a cap for fixing the septum to the channel tube unit.

14. The mixture injection port according to claim 13, wherein the plate portion of the circulating member is a substantially disk-shaped plate member, and its diameter is substantially equal to the inner diameter of the inner cavity.

15. The mixture injection port according to claim 13, wherein a protrusion is formed on a surface of the slit on the inner cavity side in the septum.

16. A method for transferring a fluid to or from a body through a mixture injection port, the mixture injection port comprising a channel tube unit including a body portion that is provided with an inner cavity and a leg portion that is provided with a narrow tube portion having a smaller width than that of the inner cavity and a septum covering one end of the channel tube unit and having a slit, the method comprising: inserting a tube member into the slit; injecting a first fluid into the tube member or a second fluid into another end of the channel tube unit; circulating, via a circulating member provided in the channel tube unit below the septum, the first fluid or the second fluid towards the septum side; and guiding, via the circulating member, the first fluid to the other end of the channel tube unit or the second fluid to a top portion of the tube member, wherein the circulating member is positioned such that a tip of the edge portion faces a gap region between the inner wall of the channel tube unit and the septum deformed by the insertion of the tube member, wherein the circulating member is separate from the channel tube unit and comprises a plate portion arranged to change direction of flow of the first fluid or the second fluid, and an edge portion that protrudes upwardly towards the septum from a periphery of the plate portion and is arranged along an inner wall of the channel tube unit, wherein the edge portion is configured to change the direction of flow of the first fluid or the second fluid towards the gap region such that at least a portion of a surface of the septum is in contact with at least a portion of the circulating first fluid redirected by the circulating plate portion to substantially flush away any stagnant matter present on said surface of the septum, and wherein an axial position of the circulating member in the channel tube unit is substantially restricted when the tube member is inserted into or pulled out of the slit, the circulating member is positioned at a step formed between the inner cavity and the narrow tube portion.

17. The method of claim 16, further comprising:
  after injecting the first fluid into the tube member or the second fluid into an other end of the channel tube unit, directing, via the circulating member, the first fluid or the second fluid radially outwardly and toward an intersection between the septum and a wall defining an inner cavity of the mixture injection port,
  wherein guiding the first fluid to the other end of the channel tube unit or the second fluid to the top portion of the tube member comprises guiding the first fluid radially inwardly towards the other end of the channel tube unit or guiding the second fluid radially inwardly towards the top portion of the tube member.

* * * * *